United States Patent
Bontoux et al.

(10) Patent No.: US 6,551,816 B1
(45) Date of Patent: Apr. 22, 2003

(54) ENZYMATIC METHOD FOR PREPARING SYNTHESIS INTERMEDIATES

(75) Inventors: Marie-Claude Bontoux, Luzinay (FR); Olivier Favre-Bulle, Lyons (FR)

(73) Assignee: Rhone-Poulenc Agro (FR)

( * ) Notice: Subject to any disclaimer, the term of this patent is extended or adjusted under 35 U.S.C. 154(b) by 0 days.

(21) Appl. No.: 09/700,379

(22) PCT Filed: May 10, 1999

(86) PCT No.: PCT/FR99/01098

§ 371 (c)(1),
(2), (4) Date: Dec. 15, 2000

(87) PCT Pub. No.: WO99/58706

PCT Pub. Date: Nov. 18, 1999

(30) Foreign Application Priority Data

May 14, 1998 (FR) .............................................. 98 06339

(51) Int. Cl.$^7$ ................................................ C12P 13/32
(52) U.S. Cl. ........................................ 435/280; 435/108
(58) Field of Search .................................. 435/280, 180

(56) References Cited

U.S. PATENT DOCUMENTS 5,552,317 A * 9/1996 Houng et al. ................ 435/280
5,552,318 A    9/1996 Houng et al.

FOREIGN PATENT DOCUMENTS

EP        0178553        1/1986
EP        0629616        12/1994

OTHER PUBLICATIONS

Chen et al., "Quantitative Analysis of Biochemicl Kinetic Rsolutions of Enantiomers" J. Am. Chem. Soc., 1982, 104 : 7294–99.*
Boland et al., "Esterolytic anc Lipolytic Enzymes in Organic Synthesis", Synthesis, Dec. 1991 : 1049–72.*
Wang et al., "Extending the applicability of esterase of low enantioselectivity in asymmetric synthesis", Enzymes in organic synthesis, Ciba Foundation Symposium 111 : 128–145 (1985).*
Aresene et al., "Biocatalysis in nonaqueous media–theoretical and practical substantiation. IV Structural and catalytic properties of enzymes in nonaqueous media", Rev. Chim. 48 (7) : 581–86 (1997).*
De Gomez–Puyou et al., "Enaymes in low water systems", Crit. Rev. Biochem. Mol. Biol. 33 (1) : 53–89 (1998).*
Svec et al., "Engineering aspects of carriers for immobilized biocatalysts", Biotechnol. Genet. Eng. Rev. 13 : 217–235 (1996).*
B. Kaptein, et al., "Enzymic Resolution of .alpha.,.alpha.–d-isubstituted.alpha.–amino acid esters and amides", *Tetrahedron: Asymmetry*, 1993, vol. 4, No. 6, pp. 1113–1116.
O. Keil, et al., "New Hydantoinases From Thermophilic Microorganisms. Synthesis of Enantiomerically Pure D–Amino Acids", *Tetrahedron: Asymmetry*, 1995, vol. 6, No. 6, pp. 1257–1260.
W.H. Pirkle, et al., "Preparation of .alpha.–substituted.alpha.–amino acids of High Enantiomeric Purity", *Chemical Abstracts*, vol. 117, No. 21, Nov. 23, 1992, Abstract No. 212925.

* cited by examiner

Primary Examiner—Irene Marx
(74) Attorney, Agent, or Firm—Ostrolenk, Faber, Gerb & Soffen, LLP

(57) ABSTRACT

The invention concerns a method for preparing α-phenylalanine ester with substantially enantiomeric purity of formulae (I) and (II) wherein Alk represents a linear or branched $C_1$–$C_6$ alkyl radical, characterized in that it consists in contacting a mixture of α-phenylalanine ester enantiomers with a lipase, a protease or an esterase.

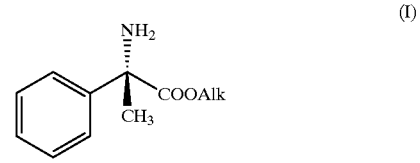

Isomère S

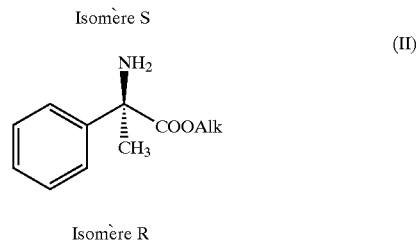

Isomère R

7 Claims, No Drawings

ENZYMATIC METHOD FOR PREPARING SYNTHESIS INTERMEDIATES

This application was filed under 35 USC 371 as the national phase of PCT/FR99/01098 filed May 10, 1999.

FIELD OF THE INVENTION

A The present invention relates to a novel method for preparing optically active synthesis intermediates for the manufacture of chemical compounds. More particularly, the present invention relates to a method for the enantiomeric enrichment of α-phenylalanine derivatives.

PRIOR STATE OF THE ART

In many fields, such as for example pharmacy and agrochemistry, active chemical compounds are increasingly complex and very frequently comprise one or more asymmetric centres. Most of these commercial products are marketed in racemate form, that is to say that all the enantiomeric and/or diastereoisomeric forms are present in the active material. However, in a very large number of cases, only one of the optically active forms possesses the desired activity, whereas the other optical isomers are inactive or can even act against the desired effect and even have risks for mammals and/or the environment. It is therefore important to be able to have methods of chemical or biochemical (enzymatic for example) synthesis which lead to the sole isomer desired. Such methods are for example asymmetric syntheses or, when the starting material is a mixture of enantiomers, the so-called enantiomeric enrichment methods.

Enzyme-catalysed enantiomeric enrichment methods are known in the literature. Among them, there may be mentioned for example the publication by B. Kaptein et al. (*Tetrahedron Asymetry*, 4(6), (1993), 1113–1116) in which the hydrolysis of an ethyl ester by a pig liver lipase is described; however, the selectivity is very poor, that is to say that the enantiomeric excess of the product is not satisfactory.

Patent WO-A-96/12035 discloses the access, by enzyme catalysis, to carboxylic acid esters possessing a high enantiomeric excess. The catalyst used is chosen from bacteria, lipases and proteases. Here again, the enantiomeric excesses observed are relatively low, and in particular in the case of the S enantiomers.

U.S. Pat. No. 5,552,318 describes a method of enriching the ethyl ester of DL-homophenylalanine with the aid of enzymes, but the enantiomeric excesses observed are highly variable. Finally patent application EP 178,553 describes an enantiomeric enrichment of amino acids by the action of α-chymotrypsin.

One subject of the present invention consists in providing an enzyme-catalysed enantiomeric enrichment method leading to a compound having a high enantiomeric excess.

One subject of the present invention consists in providing an enzyme-catalysed method of preparing a substantially enantiomerically pure compound.

Another subject of the present invention consists in providing an enzyme-catalysed method of preparing, from a mixture of enantiomers, substantially pure S enantiomer, or substantially pure R enantiomer.

Another subject of the present invention consists in providing an enzyme-catalysed method of enantiomeric enrichment from a mixture of enantiomers of esters.

Another subject of the invention consists in providing an enzyme-catalysed method of enantiomeric enrichment of a mixture of enantiomers of esters in substantially enantiomerically pure compounds, with a high yield.

It has now been discovered that all these aims can be achieved fully or partially by means of a method according to the invention, whose description is presented below.

BRIEF DESCRIPTION OF THE INVENTION

The present invention provides a novel method for the enantiomeric enrichment of α-phenylalanine esters, characterized in that a mixture of enantiomers of α-phenylalanine esters is brought into contact with an enzyme catalyst comprising unpurified or partially or completely purified enzymes. These may be used free or absorbed or immobilized on organic or inorganic supports according to methods well known to a person skilled in the art.

The substantially enantiomerically pure compounds thus obtained can serve as synthesis intermediates in the preparation of chiral active materials useful in therapy or in agriculture. By way of example, the enantiomers of α-phenylalanine esters are used as intermediates in tne preparation of certain fungicidal 2-imidazolin-5-ones and 2-imidazoline-5-thiones described ip patent EP-A-0 629 616.

DETAILED DESCRIPTION OF THE INVENTION

The present invention therefore relates to a novel method for preparing substantially enantiomerically pure α-phenylalanine esters of formulae (I) and (II)

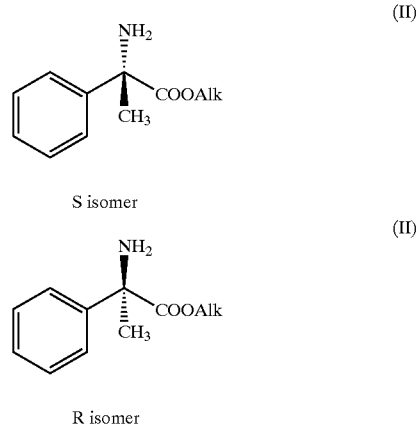

in which Alk represents a linear or branched alkyl radical containing from 1 to 6 carbon atoms, such as for example the methyl, ethyl, n-propyl, n-butyl, n-pentyl, n-hexyl, isopropyl, isobutyl, isopentyl, isohexyl, tert-butyl, tert-pentyl, tert-hexyl, neopentyl or neohexyl radical, which method is characterized in that a mixture of enantiomers of α-phenylalanine esters is brought into contact with a lipase, an esterase or a protease other than PLE (pig liver esterase), in free, absorbed or immobilized form.

The expression mixture of enantiomers is understood to mean a mixture in equal or different proportions of the S isomer of formula (I) and of the R isomer of formula (II) of the α-phenylalanine ester of formula (A):

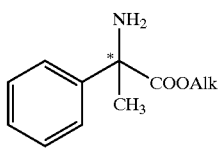

(A)

in which Alk represents a linear or branched alkyl radical containing 1 to 6 carbon atoms, as defined in the formulae (I) and (II), and the asterisk indicates the asymmetric centre of the ester.

The method according to the invention makes it possible to obtain substantially pure enantiomers, either of S configuration (ester of formula (I)), or of R configuration (ester of formula (II)).

The term "substantially pure" means that the enantiomeric excess of the enantiomer considered is greater than 80%, more particularly greater than 90%. Some enzymes used in the method according to the invention also lead to an enantiomeric excess of 100%; that is to say that, in this case, the enantiomer obtained is pure, the other enantiomeric form not being detectable.

The expression enantiomeric excess is understood to mean the ratio of the excess of the desired enantiomer relative to the undesired enantiomer.

This ratio is calculated according to one of the following equations:

$$\% \ e.e.(S) = \frac{[S] - [R]}{[R] + [S]} \times 100$$

$$\% \ e.e.(R) = \frac{[R] - [S]}{[R] + [S]} \times 100$$

in which:

%  e.e. (S) represents the enantiomeric excess in the S isomer,

%  e.e. (R) represents the enantiomeric excess in the R isomer,

[S] represents the concentration of S isomer, and

[R] represents the concentration of R isomer.

The method of the invention uses enzymes, in particular lipases, esterases and proteases.

The proteases make it possible to obtain the S enantiomer of formula (I) defined above; the lipases or esterases make it possible to obtain the R enantiomer of formula (II) defined above.

The appropriate enzymes for the method of the invention are more particularly chosen from the following enzymes which are commercially available;

| Enzyme | Supplier |
| --- | --- |
| Candida Antardca (immob.) | Novo |
| L1754 | Sigma |
| Lipase A Rhizopus | |
| Lipase CE | Amano |
| Lipase Chirazyme E1 | Boehringer |
| Lipase Chirazyme L1 | Boehringer |
| Lipase Chirazyme L2 | Boehringer |
| Lipase Chirazyme L3 | Boehringer |
| Lipase Chirazyme L4 | Boehringer |
| Lipase Chirazyme L5 | Boehringer |

-continued

| Enzyme | Supplier |
| --- | --- |
| Lipase Chirazyme L6 | Boehringer |
| Lipase Chirazyme L7 | Boehringer |
| Lipase Chirazyme L8 | Boehringer |
| Lipase GC | Amano |
| Lipase L3001 | Sigma |
| Lipase L3126 | Sigma |
| Lipase, pancreatic L115P | Sigma |
| Lipase PLE | Amano |
| Liver Acetone powder L9627 | Sigma |
| Liver porcine L8521 | Sigma |
| MAP 10 | Amano |
| Protease Biofeed | Novo |
| Protease Prozyme | Amano |
| Protease Subtilisin | Boehringer |
| Protease Subtilisin A | Novo |
| Protease Trypsin | Sigma |
| PS | Amano |
| Protease P5147 | Sigma |
| Protease P4032 (aspergillus) | Sigma |

Among the proteases, proteases from aspergillus (such as Prozyme for Amano or the protease P4032 from Sigma), Subtilisin from Boehringer of from Novo, Biofeed from Novo and trypsin.

Among the lipases and estrases, the lipases Chirazyme L2, L5, L7 and E1 from Boehringer and the lipase PLE from Amono will be more particularly preferred.

For the method according to the invention, there will be even more preferably used a protease from aspergilus or a lipase or an esterase from pigs, which are specific for one or the other of the two enantiomeric forms.

The aspergillus proteases lead specifically to the S isomer of formula (I) defined above, and among these, a protease most particularly preferred in the method of the invention is Prozyme from Amano.

The pig lipases and esterases lead, for their part, specifically to the R enantiomer of formula (II) defined above.

The enantiomeric enrichment method according to title invention therefore consists in bringing a mixture of esters of formula (A) defined above into contact with a catalytic quantity of enzyme, chosen from proteases if it is desired to obtain the S enantiomer of formula (I) defined above, or chosen from lipases or esterases fit S desired to obtain the R enantiomer of formula (II) defined above.

This reaction may be carried out under diverse and varied conditions which are well known to persons skilled in the art who are specialists in biocatalytic reactions, and are known in particular in the literature, including in "Chemical Abstracts" and computer data bases.

In general, the method is carried out in a medium having a pH of between 5 and 10. Preferably, the reaction occurs at the optimum pH defined by the supplier of the enzyme.

The reaction is carried out at a temperature generally of between 4° C. and 70° C. Preferably, the temperature is the optimum temperature defined by the supplier of the enzyme.

The duration of the reaction has a direct effect on the rate of conversion and is generally between 1 and 120 hours, more preferably between 10 and 60 hours, depending on the reaction temperature and the nature of the enzyme used.

The values for the pH, temperature and duration of reaction which are given here are those generally selected, but it is clearly understood that the operating conditions will be adapted to each specific reaction.

The method according to the invention may be carried out in the presence or in the absence of water, in the presence or in the absence of one or more solvents or in the presence of water and one or more solvents. In general, these solvents are compatible with the enzymatic activity and are chosen from those which solubilize the ester of formula (A). According to a most particularly preferred aspect of the invention, these solvents are chosen from aromatic solvents. More preferably still, the solvents are for example toluene or monochlorobenzene.

The ratio by volume of the quantity of solvent used relative to the quantity of water is generally between 5% and 90%, preferably between 20% and 80%.

The method described above is generally carried out with the enzyme and the mixture of enantiomers being present in a homogeneous or heterogeneous phase.

One variant of the method according to the invention consists in using, in a corresponding and appropriate quantity, the enzyme immobilized on a support, according to methods well known to a person skilled in the art, such as for example those described in K. H. Lee et al., *J. Chem. Tech. Biotechnol.*, 54, (1992), 375–382.

The esters of formula (I) and (II) defined above, which are obtained according to the method of the invention, find a most particularly advantageous application as synthesis intermediates in the preparation of chiral active materials useful in particular in therapy or in agriculture.

For example, the esters of formula (I) and (II) may be used as intermediates in the preparation of certain fungicidal 2-imidazolin-5-ones and 2-imidazoline-5-thiones described in patent EP-A-0 629 616 of formula (F):

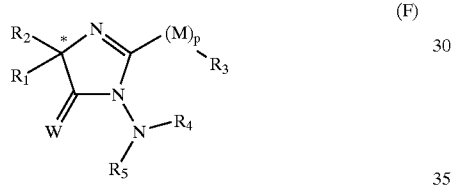

(F)

in which $R_1$ represents the phenyl radical and $R_2$ represents the methyl radical and W represents an oxygen or sulphur atom, or a group S=O;

M represents an oxygen or sulphur atom, or a $CH_2$ radical, optionally halogenated;

p is an integer equal to 0 or 1;

$R_3$ represents:
a hydrogen or an optionally halogenated $C_1$–$C_2$ alkyl radical, when p equals 0 or $(M)_p$ is a $CH_2$ radical,
an optionally halogenated $C_1$–$C_2$ alkyl radical, when $(M)_p$ represents an oxygen or sulphur atom;

$R_4$ represents:
the hydrogen atom, or
an alkyl radical containing from 1 to 6 carbon atoms, or
an alkoxyalkyl, alkylthioalkyl, haloalkyl, cyanoalkyl, thiocyanatoalkyl, alkenyl or alkynyl radical containing from 2 to 6 carbon atoms, or
a dialkylaminoalkyl, alkoxycarbonylalkyl or N-alkylcarbamoylalkyl radical containing from 3 to 6 carbon atoms, or
an N,N-dialkylcarbamoylalkyl radical containing from 4 to 6 carbon atoms, or
an aryl radical comprising phenyl, naphthyl, thienyl, furyl, pyridyl, pyrimidyl, pyridazinyl, pyrazinyl, benzothienyl, benzofuryl, quinolyl, isoquinolyl, or methylenedioxyphenyl, optionally substituted with 1 to 3 groups chosen from $R_6$, or
an arylalkyl, aryloxyalkyl, arylthioalkyl or arylsulphonylalkyl radical, the terms aryl and alkyl having the definitions given above;

$R_5$ represents:
hydrogen, or an alkyl, haloalkyl, alkylsulphonyl or haloalkylsulphonyl radical containing from 1 to 6 carbon atoms, or
an alkoxyalkyl, alkylthioalkyl, acyl, alkenyl, alkynyl, haloacyl, alkoxycarbonyl, haloalkoxycarbonyl, alkoxyalkylsulphonyl or cyanoalkylsulphonyl radical containing from 2 to 6 carbon atoms, or
an alkoxyalkoxycarbonyl, alkylthioalkoxycarbonyl or cyanoalkoxycarbonyl radical containing from 3 to 6 carbon atoms, or
the formyl radical or a cycloalkyl, alkoxyacyl, alkylthioacyl, cyanoacyl, alkenylcarbonyl or alkynylcarbonyl radical containing from 3 to 6 carbon atoms, or
a cycloalkylcarbonyl radical containing from 4 to 8 carbon atoms, or
a radical phenyl; arylalkylcarbonyl, in particular phenylacetyl and phenylpropionyl, arylcarbonyl, in particular benzoyl, optionally substituted with 1 to 3 groups from $R_6$, thienylcarbonyl, furylcarbonyl, pyridylcarbonyl, benzyloxycarbonyl, furfuryloxycarbonyl, tetrahydrofurfuryloxycarbonyl, thienylmethoxycarbonyl, pyridylmethoxycarbonyl, phenoxycarbonyl or phenylthiocarbonyl, the phenyl radical being itself optionally substituted with 1 to 3 groups chosen from $R_6$, alkylthiocarbonyl, haloalkylthiocarbonyl, alkoxyalkylthiocarbonyl, cyanoalkylthiocarbonyl, benzylthiocarbonyl, furfurylthiocarbonyl, tetrahydrofurfurylthiocarbonyl, thienylmethylthiocarbonyl, pyridylmethylthiocarbonyl or arylsulphonyl, or
a carbamoyl radical optionally mono- or disubstituted with:
an alkyl or haloalkyl group containing from 1 to 6 carbon atoms,
a cycloalkyl, alkenyl or alkynyl group containing from 3 to 6 carbon atoms,
an alkoxyalkyl, alkylthioalkyl or cyanoalkyl group containing from 2 to 6 carbon atoms, or
a phenyl optionally substituted with 1 to 3 groups $R_6$;
a sulphamoyl group optionally mono- or disubstituted with:
an alkyl or haloalkyl group containing from 1 to 6 carbon atoms,
a cycloalkyl, alkenyl or alkynyl group containing from 3 to 6 carbon atoms,
an alkoxyalkyl, alkylthioalkyl or cyanoalkyl group containing from 2 to 6 carbon atoms, or
a phenyl optionally substituted with 1 to 3 groups $R_6$;
an alkylthioalkylsulphonyl group containing from 3 to 8 carbon atoms or a cycloalkylsulphonyl group containing from 3 to 7 carbon atoms;

$R_4$ and $R_5$, taken together, can also form with the nitrogen atom to which they are attached a pyrrolidino, piperidino, morpholino or piperazino group optionally substituted with an alkyl radical containing from 1 to 3 carbon atoms.

$R_6$ represents:
a halogen atom, or
an alkyl, halbalkyl, alkoxy, haloalkoxy, alkylthio, haloalkylthio or alkylsulphonyl radical containing from 1 to 6 carbon atoms, or
a cycloalkyl, halocycloalkyl, alkenyloxy, alkynyloxy, alkenylthio or alkynylthio radical containing from 3 to 6 carbon atoms, or the nitro or cyano group, or an amino radical optionally mono- or disubstituted with an alkyl or acyl radical containing from 1 to 6 carbon atoms or an alkoxycarbonyl radical containing from 2 to 6 carbon atoms, a phenyl, phenoxy or pyridyloxy radical, it being possible for these radicals to be optionally substituted with 1 to 3 groups, which are identical or different, chosen from $R_7$, $R_7$ represents:

a halogen atom chosen from fluorine, chlorine, bromine or iodine, or an alkyl radical containing from 1 to 6 carbon atoms, or an alkoxy or alkylthio radical containing from 1 to 6 carbon atoms, or a haloalkoxy or haloalkylthio radical containing from 1 to 6 carbon atoms, or a nitrile or nitro radical.

The method for preparing the compounds of formula (F) may be represented by the following scheme:

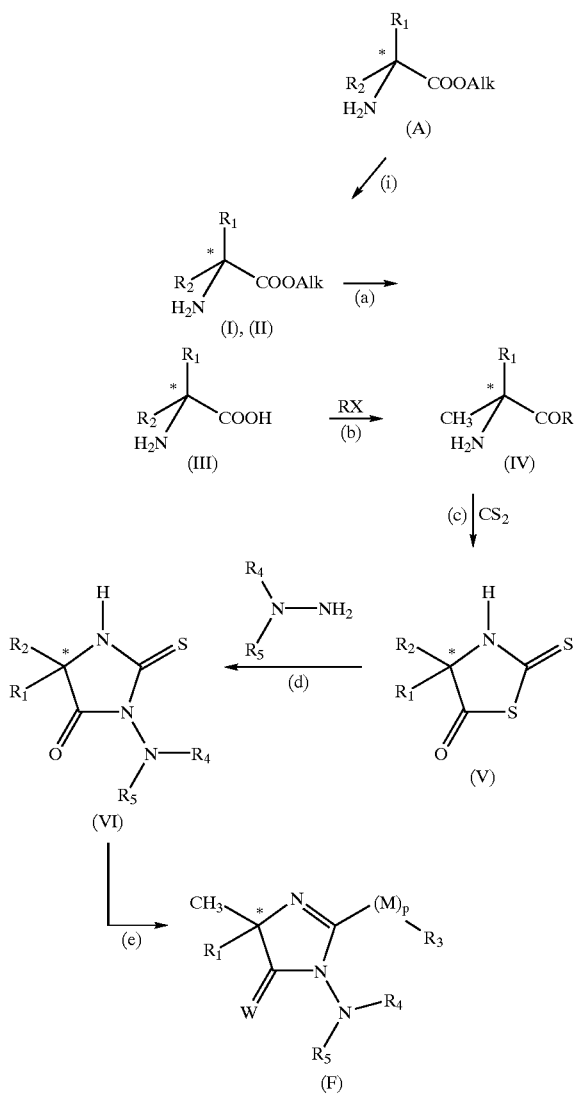

in which scheme, the radicals Alk, $R_1$, $R_2$, $R_3$, $R_4$, $R_5$, M, p and W are as defined above, R represents a hydroxyl radical, an alkoxy radical containing from 1 to 6 carbon atoms, a benzyloxy radical, an amino, alkylamino or dialkylamino radical, an alkylamino radical containing from 1 to 6 carbon atoms, and X represents a leaving group such as a halogen atom, chosen from chlorine, bromine and iodine, or a sulphate, or alkylsulphonyloxy or arylsulphonyloxy radical.

In the preceding scheme step (i) is the method of the present invention and is exemplified in the text which follows in the present description;

step (a) is a conventional saponification step;

steps (b), (c) and (d) are described in patent WO-98/03490, the details of which are incorporated here by reference (b) is an esterification, (c) is a cyclization and (d) is a catalyzed amine addition;

step (e) is described in patent EP-A-0 629 616, the details of which are incorporated here by reference and constitutes incorporating $R_3$ into the compound by addition of $R_3X$ or $R_3OH$, with possible optional oxidation.

It is clearly understood that when the radical R represents the radical OAlk, steps (a) and (b) are superfluous and it is possible not to carry them out in this general synthesis scheme.

The overall method for the synthesis of the compounds of formula (F), from amino acids of formula (A) via the intermediates of formulae (I) and (II), is novel and in this regard is included in the scope of the present invention.

The implementation of the enantiomeric enrichment method according to the invention is illustrated by the following representative examples; these examples in no case provide a limitation to the characteristics of the present invention.

EXAMPLE 1

250 mg of aspergillus protease (Amano Prozyme 6) and 5 ml of 100 mM phosphate buffer containing 50 mM of a racemic mixture of methyl esters of α-phenylalanine are successively loaded into a magnetically stirred tube for weighing materials.

After 17 hours of reaction at 30° C., the enantiomeric excess of the residual ester is measured by chiral HPLC (High-Performance Liquid Chromatography). A residual ester of S configuration with an enantiomeric excess of 99.4% is found.

EXAMPLES 2 TO 5

By repeating Example 1 above and replacing the protease Prozyme 6 from Amano with other enzymes, the following results are obtained:

| Example | Enzyme | Configuration of the residual ester | Enantiomeric excess |
|---|---|---|---|
| 2 | Subtilisin (Boehringer) | S | 79.5 |
| 3 | Subtilisin a (Novo) | S | 80.5 |
| 4 | Protease P4032 | S | 100 |
| 5 | Esterase E1 (Boehringer) | R | 71 |

EXAMPLE 6

0.2 g of protease Prozyme, 2.5 ml of 100 mM phosphate buffer (pH 7), 2.5 ml of toluene and 0.223 g of a racemic mixture of methyl esters of α-phenylalanine are successively loaded into a magnetically stirred tube for weighing materials.

After 120 hours of reaction at 30° C., the organic phase is recovered and evaporated off. The residual methyl ester is taken up in the chiral HPLC eluent and then injected onto an AGP column. The enantiomeric excess of the residual ester of S configuration is 80%.

What is claimed is:

1. Method for preparing substantially enantiomerically pure α-phenylalanine esters of formula (I) or (II):

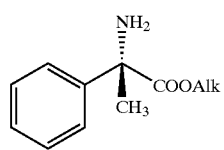
(I)

S isomer

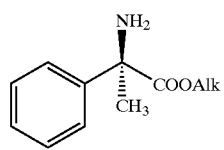
(II)

R isomer in which Alk represents a linear or branched alkyl radical containing from 1 to 6 carbon atoms, wherein a mixture of enantiomers of α-phenylalanine esters is brought into contact with a protease or an esterase.

2. Method according to claim 1, wherein the substantially enantiomerically pure ester is of S configuration and the enzyme used is a protease.

3. Method according to claim 2, in which the protease is selected from the group consisting of Aspergillus protease P4032, Aspergillus Prozyme, and subtilisin.

4. Method according to claim 1, in which the esterase is pig liver esterase.

5. A method for the preparation of a fungicidal 2-imidazolin-5-one or 2-imidazolin-5-thione which comprises effecting the method of claim 1;

cyclizing the resulting ester using $CS_2$;

effecting a catalyzed amine addition to the cyclized product; and converting the S moiety of the resulting product to a —$(M)_p$—$R_3$ moiety in which M is oxygen, sulfir or an optionally halogenated methylene group and p is 0 or 1, and in which $R_3$ is (a) hydrogen or an optionally halogenated $C_{1-2}$ alkyl radical when p is 0 or $(M)_p$ is methylene or (b) an optionally halogenated methyl group or is an optionally halogenated $C_{1-2}$ alkyl radical when $(M)_p$ is oxygen or sulfur and p is 1.

6. Method according to claim 1, in which "Alk" represents the methyl or ethyl radical.

7. Method according to claim 1, further wherein the reaction medium has a pH between 5 and 10 and the reaction temperature is between 4° C. and 70° C.

* * * * *